United States Patent
Enderle et al.

(10) Patent No.: US 9,915,650 B2
(45) Date of Patent: Mar. 13, 2018

(54) METHOD OF DETECTION OF CAMP AND CGMP VIA A FLUOROPHORE AND DEQUENCHER COMPLEX

(75) Inventors: Thilo Enderle, Rheinfelden (DE); Hugues Matile, Basel (CH); Doris Roth, Basel (CH)

(73) Assignee: HOFFMANN-LA-ROCHE INC., Nutley, NJ (US)

( * ) Notice: Subject to any disclaimer, the term of this patent is extended or adjusted under 35 U.S.C. 154(b) by 266 days.

(21) Appl. No.: 11/955,415

(22) Filed: Dec. 13, 2007

(65) Prior Publication Data

US 2008/0153123 A1 Jun. 26, 2008

(30) Foreign Application Priority Data

Dec. 21, 2006 (EP) .................................. 06126927

(51) Int. Cl.
 *C12Q 1/68* (2006.01)
 *G01N 33/542* (2006.01)
 *G01N 33/573* (2006.01)

(52) U.S. Cl.
 CPC ............. *G01N 33/542* (2013.01); *C12Q 1/68* (2013.01); *G01N 33/5735* (2013.01)

(58) Field of Classification Search
 None
 See application file for complete search history.

(56) References Cited

U.S. PATENT DOCUMENTS

2004/0203000 A1* 10/2004 Sportsman et al. ............. 435/6

FOREIGN PATENT DOCUMENTS

| EP | 1181059 | 2/2002 |
|---|---|---|
| EP | 1502961 | 2/2005 |
| WO | 2003/078449 | 9/2003 |
| WO | 2003/089014 | 10/2003 |
| WO | WO 03089014 A1 * | 10/2003 |
| WO | 2006/093529 | 9/2006 |

OTHER PUBLICATIONS

Moll et al., Biomolecular interaction analysis in functional proteomics, J Neural Transm (2006) 113: 1015-1032, published online Jul. 13, 2006.*
Hiratsuka, New Fluorescent Analogs of cAMP and cGMP Available as Substrates for Cyclic Nucleotide Phosphodiesterase, The journal of Biological Chemistry, vol. 257. No. 22, Issue of Nov. 25, pp. 13354-13358. 1982.*
Kraemer, A. et al, *Jour. of Molecular Biology*, vol. 306(5), 1167-1177 (2001).
Williams, C., *Nature Reviews*, Drug Discovery, vol. 3(2), 125-135 (2004).
Gabriel, D. et al, *Assay and Drug Development Tech*, vol. 1(2), 291-303 (2003).
Campbell, A. et al *Biochem. Jour.*, vol. 216(1), 185-194 (1983).
Moll, D. et al, *Jour. of Neural Transmission*, vol. 113(8), 1015-1032 (2006).
Thomsen, W. et al, *Curr. Opin. in Biotechnology*, (2005) 16, 655-665.

* cited by examiner

*Primary Examiner* — Prabha Chunduru

(57) ABSTRACT

The present invention relates to an in vitro method for detecting cAMP or cGMP comprising a) contacting a mixture with a complex of a tracer and a dequencher, wherein the tracer is a fluorophore covalently linked to a cAMP quencher, and b) measuring the change in fluorescence. Furthermore, the present invention relates to the use of said method for determining the cAMP or cGMP concentration in the mixture, for determining the activity of a receptor wherein the signal transduction of the receptor comprises cAMP or cGMP and for screening of a ligand for such a receptor.

4 Claims, 15 Drawing Sheets

Figure 1 –
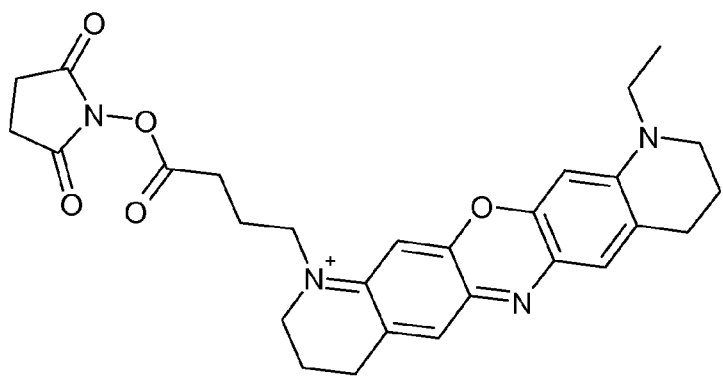
Figure 2
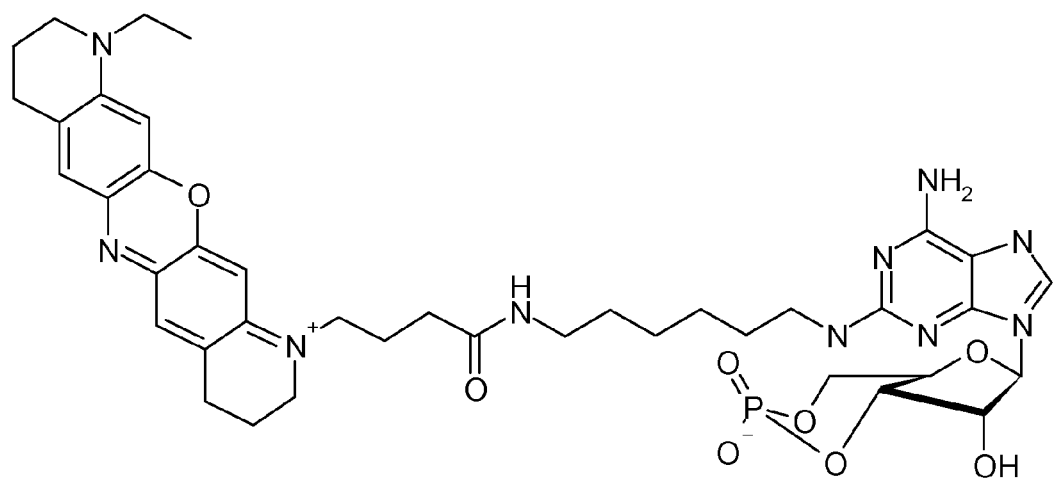

US 9,915,650 B2

METHOD OF DETECTION OF CAMP AND CGMP VIA A FLUOROPHORE AND DEQUENCHER COMPLEX

PRIORITY TO RELATED APPLICATION(S)

This application claims the benefit of European Patent Application No. 06126927.0, filed Dec. 21, 2006, which is hereby incorporated by reference in its entirety.

BACKGROUND OF THE INVENTION

Nucleotides play an important role in the signal transduction of a cell. For example, the nucleotide cAMP is involved in the signal transduction of G-protein-coupled receptors (GPCRs). GPCRs form the largest class of pharmaceutical drug targets. In order to test the activity of potential new medicines on GPCRs in drug discovery, assays are needed which monitor the function of the receptors in their cellular environment. For high throughput screening, very early in the drug discovery process, these functional assays need to be simple with a low number of steps, sensitive to detect minute effects of early compounds and they need to comprise a robust readout to be applied in an automated fashion.

Functional assays for GPCRs can be set-up by detection of second messenger molecules reflecting the activation state of the receptor. Such a second messenger molecule is cyclic adenosine monophosphate (cAMP) formed upon modulation of the adenylyl cyclase activity. An overview on commercially available, functional assay kits that determine the level of cellular cAMP based on fluorescence or chemiluminescence readout is given by W. Thomsen et al. (*Current Opinion in Biotechnology* 2005, 16, 655-665). These kits are time-consuming and complex in operation and number of steps.

SUMMARY OF THE INVENTION

Therefore, the present invention provides a simple assay for detecting cAMP and its use for indirectly detecting receptor activity and for screening of ligands.

This invention is based on the surprising fact that conjugates with cAMP derivates designed by modification of the nucleobase can quench the fluorescence emission of a fluorophore while cAMP does not quench the fluorophore.

Therefore, the present invention provides an in vitro method for detecting cAMP in a mixture comprising a) contacting a mixture comprising cAMP with a complex of a tracer and a dequencher, wherein the tracer is a fluorophore covalently linked to a cAMP quencher, and b) measuring the change in fluorescence.

Surprisingly, the assay can also be used to detect cGMP in a mixture. Unlike cAMP, cGMP has quenching capabilities, but only in a concentration of about 1 mM and above. However, cellular cGMP concentrations are usually in the range of several orders of magnitude below 1 mM.

Therefore, the present invention provides an in vitro method for detecting cAMP or cGMP in a mixture comprising a) contacting a mixture comprising cAMP or cGMP with a complex of a tracer and a dequencher, wherein the tracer is a fluorophore covalently linked to a cAMP quencher, and b) measuring the change in fluorescence.

DESCRIPTION OF THE FIGURES

FIG. 1 shows the molecular structure of the fluorophore MR121 as NHS ester as it was used for labeling of the cAMP derivative in the examples.

FIG. 2 shows the molecular structure of MR121-2-AHA-cAMP.

DETAILED DESCRIPTION

Therefore, the present invention provides a simple assay for detecting cAMP and its use for indirectly detecting receptor activity and for screening of ligands.

This invention is based on the surprising fact that conjugates with cAMP derivates designed by modification of the nucleobase can quench the fluorescence emission of a fluorophore while cAMP does not quench the fluorophore.

Therefore, the present invention provides an in vitro method for detecting cAMP in a mixture comprising a) contacting a mixture comprising cAMP with a complex of a tracer and a dequencher, wherein the tracer is a fluorophore covalently linked to a cAMP quencher, and b) measuring the change in fluorescence.

Surprisingly, the assay can also be used to detect cGMP in a mixture. Unlike cAMP, cGMP has quenching capabilities, but only in a concentration of about 1 mM and above. However, cellular cGMP concentrations are usually in the range of several orders of magnitude below 1 mM.

Therefore, the present invention provides an in vitro method for detecting cAMP or cGMP in a mixture comprising a) contacting a mixture comprising cAMP or cGMP with a complex of a tracer and a dequencher, wherein the tracer is a fluorophore covalently linked to a cAMP quencher, and b) measuring the change in fluorescence.

Preferably, the measured change of the fluorescence is compared with a control. The control may, for example, be a standard curve with predetermined amount of nucleotide.

A. Definitions

The term "mixture" refers to two or more substances mixed together in such a way that each remains unchanged. The mixture includes but is not restricted to cell lysates, cell culture supernatants, biological fluids such as serum, plasma, urine, bronchial lavage fluid, sputum, biopsies like cerebrospinal fluid.

The term "nucleotide" refers to a molecule comprising a nucleobase, a sugar, and one (MP), two (DP) or three (TP) phosphate groups. There are five nucleobases: Adenine (A), Uracil (U), Thymine (T), Guanine (G) and Cytosine (C). The sugar is either a ribose or a desoxyribose (d).

The term "cyclic nucleotide" refers to a nucleotide in which the phosphate group is bonded to two of the sugar's hydroxyl groups, forming a cyclical or ring structure. These include cyclic AMP (cAMP), cyclic CMP (cCMP), cyclic TMP (cTMP), cyclic UMP (cUMP) and cyclic GMP (cGMP).

Figure 11A:
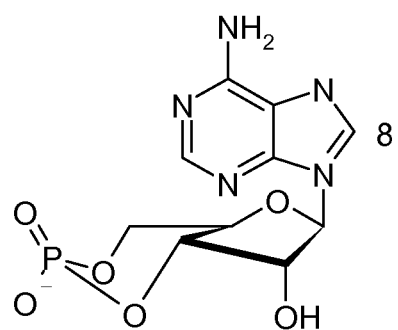
FIG. 11 shows the chemical structure of cyclic adenosine monophosphate (cAMP) (A) and the purine ring of cAMP (B).
Figure 11B:
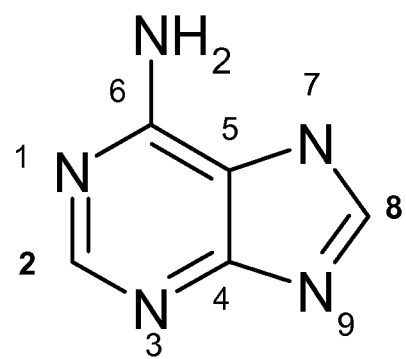
Figure 12A:
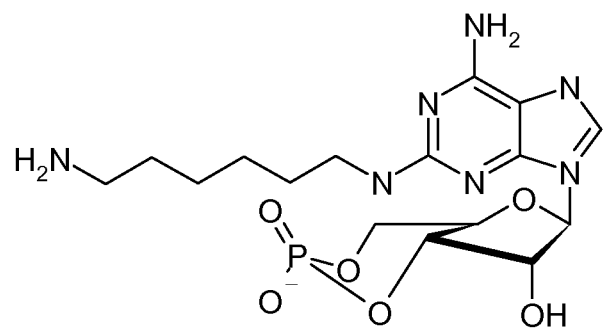
FIG. 12 shows the chemical structures of cAMP derivates
A): 2-(6-Aminohexyl)amino-cAMP (2-AHA-cAMP),
B): 8-Hydroxy-cAMP (8-OH-cAMP)
C): 8-(4-Mercaptobutylthio)-cAMP (8-MBT-cAMP)
D): 8-(8-Amino-3,6-dioxaoctylamino) (8-ADOA-cAMP)
E): 8-(6-Aminohexyl)amino-cAMP (8-AHA-cAMP)
F): N-6-Aminohexyl-cAMP
G): 2'-AEC-cAMP (AEC=3-Amino-9-ethyl carbazole)
Figure 12B:
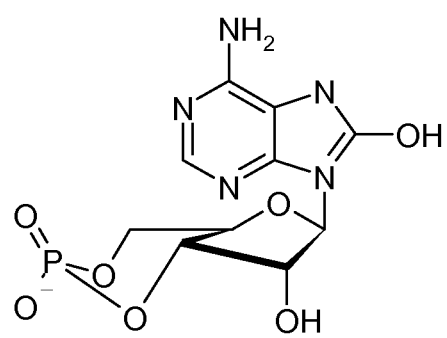
Figure 12C:
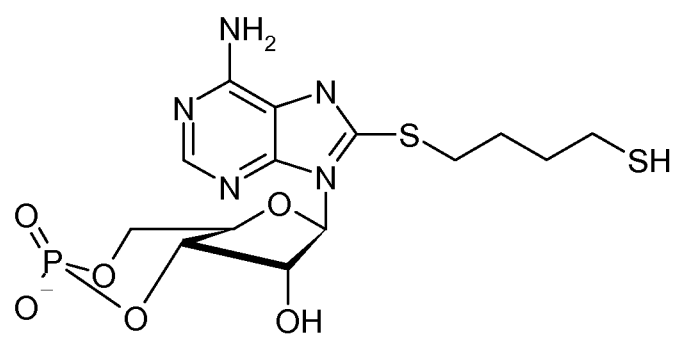
Figure 12D:
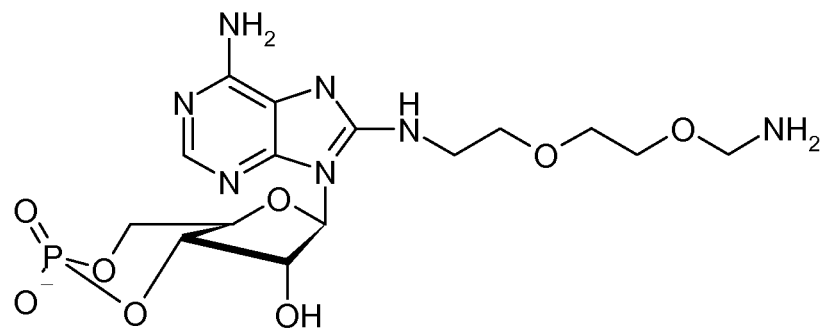
Figure 12E:
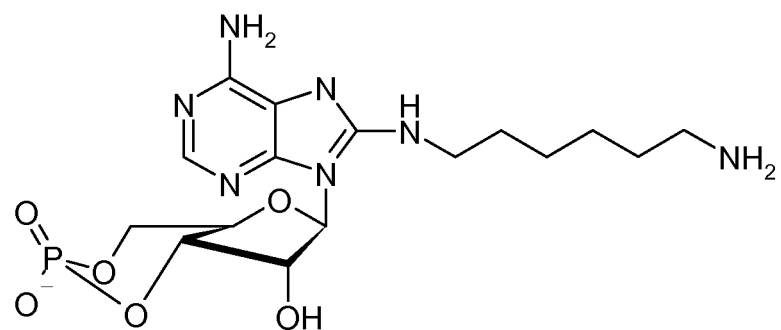
Figure 12F:
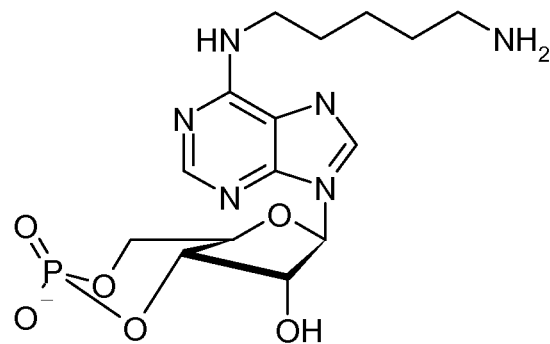
Figure 12G:
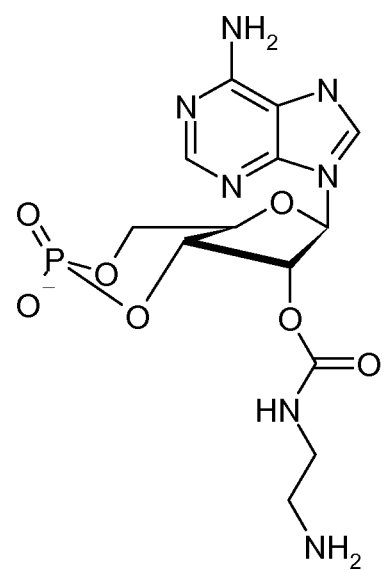

The term "cAMP quencher" as used herein refers to a derivate of cAMP which is able to quench the fluorophore used in the assay. The quencher is covalently linked to said fluorophore. The cAMP quencher is a derivate of cAMP whereby the nucleobase is substituted with an electron donor. The position of the nucleobase for a substitution is position 2 or 8 as shown in FIG. 11B. Preferred derivates of cAMP are 2-(6-Aminohexyl)amino-cAMP (2-AHA-cAMP), 8-(6-Aminohexyl)amino-cAMP (8-AHA-cAMP), 8-(8-Amino-3,6-dioxaoctylamino)-cAMP (8-ADOA-cAMP), 8-Hydroxy-cAMP (8-OH-cAMP), 8-(4-Mercaptobutylthio)-cAMP (8-MBT-cAMP). The most preferred derivative is 2-AHA-cAMP.

The term "fluorophore" refers to a molecule emitting fluorescence when excited with a specific wavelength and being statically quenchable. A preferred fluorophore is an oxazine derivate as described in EP 747 447 such as for example MR121, Evoblue30 or JA314 (2H -Dipyrido[3,2-b:2',3'-i]phenoxazin-13-ium, 1-[4-[(2,5-dioxo-1-pyrrolidinyl)oxy]-4-oxobutyl]-11-sulfobutyl-3,4,8,9,10,11-hexahydro). Further preferred fluorophores which may be used are ATTO 590, ATTO 655, ATTO 680, ATTO 700 (Atto-Tec GmbH, Am Eichenhang 50, 57076 Siegen, Germany). More preferably, the fluorophore is MR121 or ATTO 700.

The term "dequencher" as used herein refers to a molecule which reverses the quenching effect of the cAMP quencher by binding to the cAMP quencher. It is essential that the dequencher is able to bind the cAMP quencher as well as the cyclic nucleotide which shall be detected i.e. cAMP or cGMP.

The dequencher may be a binding protein. Preferably, the dequencher is a cAMP-specific antibody. The antibody may be a monoclonal or a polyclonal antibody. If the dequencher is a protein, the pH value has to be adapted to a range in which the protein is capable of binding. Normally, this range is pH 6.8 to 7.8.

Methods for producing antibody which are specific for a nucleotide are well known to the skilled in the art. Kohler and Milstein (*Nature* 1975, 256: 495-497), for example, describe methods for producing monoclonal antibodies.

The "detection complex" comprises a tracer and a dequencher. The tracer consists of a fluorophore covalently linked to a cAMP quencher. The detection complex shows fluorescence if excited. When the detection complex is contacted with a nucleotide, the dequencher binds a certain percentage of the free nucleotide and leaves the detection complex. The tracer is now not anymore dequenched and shows only low or no fluorescence when excited. This decrease of the fluorescence is indicative for the amount of nucleotide present in the system.

The term "ligand" as used herein refers to a molecule that binds to a receptor. A ligand may be an agonist, an antagonist, a modulator, partial agonist or a partial antagonist.

The term "agonist" refers to a molecule that binds to a receptor and triggers a response in the cell. The term "partial agonist" refers to a molecule that partially activates a receptor. The term "antagonist" refers to a molecule that binds to the receptor but fails to activate the receptor and actually blocks it from activation by an agonist.

The change of fluorescence may be compared with a control such as, for example, a standard curve. A standard curve may be established by measuring the change in fluorescence for predetermined amounts of the nucleotide which shall be detected.

B. Detailed Description

The present invention further provides the use of the methods as described above for determining the cAMP concentration in a mixture. Furthermore, the methods as described above may be used for determining the activity of receptors wherein the signal transduction of these receptors comprises cAMP or cGMP. Preferably, the receptor is a G-protein coupled receptor (GPCR).

Therefore, the present invention also provides a method for determining the activity of a receptor, wherein the signal transduction of this receptor comprises cAMP or cGMP, comprising a) contacting cells expressing the said receptor with a complex of a tracer and a dequencher, wherein the tracer is a fluorophore covalently linked to a cAMP quencher,
b) lysing the cells and
c) measuring the change in fluorescence.
Alternatively, step b) can be prior to step a).

A preferred embodiment is a method for determining the activity of a GPCR comprising
a) contacting cells expressing the GPCR with a complex of a tracer and a dequencher, wherein the tracer is a fluorophore covalently linked to a cAMP quencher, b) lysing the cells and
c) measuring the change in fluorescence.
Alternatively, step b) can be prior to step a).

Preferably, the measured change of the fluorescence is compared with a control. The control may, for example, be a standard curve with predetermined amount of cAMP or cGMP.

Furthermore, the present invention provides the use of the methods as described above for screening ligands of a receptor wherein the signal transduction of this receptor comprises cAMP or cGMP. Preferably, said receptor is a GPCR.

Therefore, the present invention also provides a method for screening a ligand for a receptor, wherein the signal transduction of this receptor comprises cAMP or cGMP, comprising:
a) contacting a candidate compound with cells expressing said receptor,
b) adding a complex of a tracer and a dequencher, wherein the tracer is a fluorophore covalently linked to a cAMP quencher,
c) lysing the cells and
d) measuring the change in fluorescence.
Alternatively, step c) can be prior to step b).

A preferred embodiment is a method for screening a ligand for a GPCR comprising
a) contacting a candidate compound with cells expressing said GPCR
b) adding to the cells a complex of a tracer and a dequencher, wherein the tracer is a fluorophore covalently linked to a cAMP quencher,
c) lysing the cells
d) measuring the change in fluorescence.
Alternatively, step c) can be prior to step b).

Preferably, the measured change of the fluorescence is compared with a control. The control may, for example, be a standard curve with predetermined amount of nucleotide.

A cell expressing a receptor such as for example GPCR may be a cell which expresses said receptor endogenously or a cell transgenic for said receptor.

Such transgenic cell maybe created by methods known in the art. A preferred method comprises the following steps: cloning a DNA which encodes the receptor of interest, inserting said DNA into a vector and introducing said vector into the cell. Preferably, said vector comprises stretches which are homologous to stretches in the genome of the cell suitable for homologous recombination and thereby allowing the targeted insertion of the DNA encoding the receptor into the genome of the cell.

The present invention also relates to a kit comprising a dequencher and a fluorophore covalently linked with cAMP quencher as described above. The kit may comprise the dequencher and the modified fluorophore separately or in a complex.

The kit may also comprise any other components deemed appropriate in the context of measuring the level(s) of the respective fluorophores, such as suitable buffers, filters, etc. Optionally, the kit may additionally comprise a user's manual for interpreting the results of any measurement(s) with respect to determining the GPCR activity. Particularly, such manual may include information for the interpretation of the measured change in fluorescence, preferably a standard curve.

Having now generally described this invention, the same will become better understood by reference to the specific examples, which are included herein for purpose of illustration only and are not intended to be limiting unless otherwise specified, in connection with the aforementioned figures.

EXAMPLES

Commercially available reagents referred to in the examples were used according to manufacturer's instructions unless otherwise indicated.
Reagents and Instrumentation cAMP, cGMP, 2-AHA-cAMP, 8-AHA-cAMP, 8-ADOA-cAMP, 2'-AEC-cAMP, 8-MBT-cAMP, N-6-Aminohexyl-cAMP and 8-OH-cAMP were purchased from Biolog Life Science Institute (28071 Bremen, Germany), MR121 NHS ester and N-6-Aminohexyl-cAMP from Roche diagnostics (Penzberg, Germany) and Atto 700 NHS ester from Atto-Tec GmbH (Atto-Tec GmbH, Am Eichenhang 50, 57076 Siegen, Germany). Monoclonal mouse anti-cAMP antibodies were produced in-house as described by Kohler and Milstein (*Nature* 1975, 256: 495-497)

All experiments were performed in PBS (pH 7.4) containing 0.1% BSA (Albumin, bovine serum, ≥96%, essentially fatty acid free, A6003, Sigma-Aldrich Chemie GmbH, Industriestrasse 25, CH-9471 Buchs, Switzerland). To lyse the cells a 3× PBS lysis buffer (pH 7.4) was used containing 0.1% BSA (Albumine from bovine serum, fraction V, ≥96%, 05480, Sigma-Aldrich Chemie GmbH), 0.45% Triton® X-100 (9342, Sigma-Aldrich Chemie GmbH), 0.075% NP40 (Nonidet P40 Substitute, 19628, USB Corporation, Cleveland, Ohio USA) and 0.3‰ $NaN_3$ (purum p.a., ≥99%, 71290, Sigma-Aldrich Chemie GmbH). Growth medium for the cells was F-12K (Gibco 21127-002) with 10% FCS and 1% Penicillin-Streptomycin (Gibco 15140-122).

All fluorescence intensity measurements were carried out by means of a plate:vision fluorescence reader (Evotec Technologies GmbH, Schnackenburgallee 114, D-22525 Hamburg, Germany) equipped with a high pressure Xe arc lamp using for the measurements with MR121 an excitation filter at 630 nm (bandwidth 50 nm) and an emission filter at 695 nm (bandwidth 55 nm) and for the measurements with Atto 700 an excitation filter at 655 nm (bandwidth 50 nm) and an emission filter at 710 nm (bandwidth 40 nm). The fluorescent intensity was adjusted to about 60% of the maximal signal of the employed iCCD camera by using attenuation filters and varying exposure times. The lifetime measurements were performed by means of a plate:vision TRF reader (Evotec Technologies GmbH, Schnackenburgallee 114, D-22525 Hamburg, Germany) with an OPO system as light source (GWU Lasertechnik Vertriebsgesellschaft m.b.H., 50374 Erftstadt, Germany) tuned to 630 nm for excitation and the emission filter at 695 nm.

All experiments were done in 384 well microtiter plates (Costar 384, black with clear, flat bottom, tissue culture treated, Prod. No.3712), the total assay volume varying from 30 to 40 µl.

Example 1

Quenching of MR121

1.1 Quenching Capabilities of Cyclic Nucleotides

Figure 13:
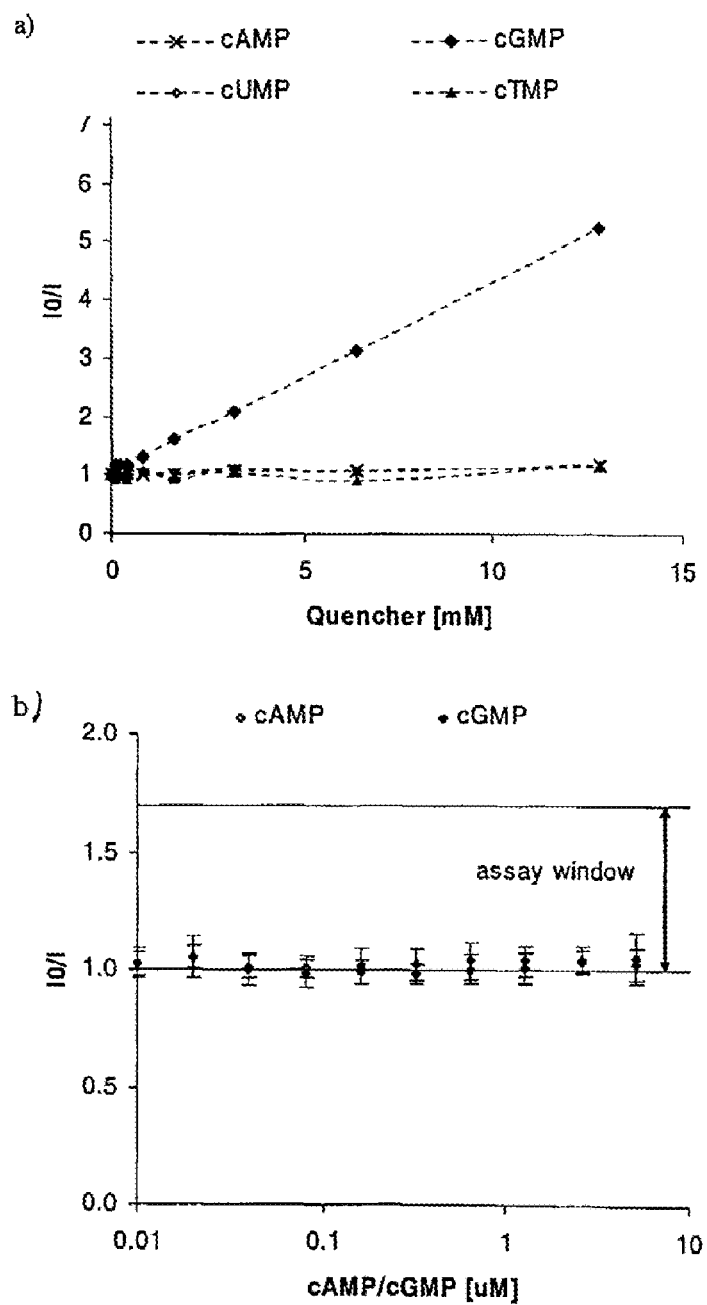
FIG. 13 shows a graphical representation of the quenching of MR121 by cAMP, cGMP, cUMP and cTMP up to 13 mM (a). (b) shows a graphical representation of the quenching of MR121 by cAMP and cGMP in the concentrations up to 10 µM in a Stern-Vollmer Plot. In low concentrations, neither cAMP nor cGMP quenches MR121.

20 µl MR121 (in PBS, end concentration 20 nM) and 20 µl quencher in PBS (DMSO end concentration in the assay: 1.25%) were pipetted into a microtiter plate. Fluorescence and lifetime were measured after an incubation time of 30 minutes at RT. The tested concentrations of the cyclic nucleotides were 0, 0.1, 0.2, 0.4, 0.8, 1.6, 3.2, 6.4 and 12.8 mM.

cGMP quenches MR121 at higher concentrations (FIG. 13a). However, this quenching does not affect the assay window because such concentrations are not reached in a cGMP assay. In low concentrations up to 10 µM (corresponds to range of cellular concentrations), neither cAMP nor cGMP quench the fluorophore (FIG. 13b). In the displacement assay with the MR121-2-AHA-cAMP tracer the assay window for displacement with cAMP or cGMP goes from 1 (MR121-2-AHA-cAMP dequenched upon binding to the antibody) to 1.7 I/I$_0$ (MR121 quenched by 2-AHA-cAMP).

1.2 Quenching with cAMP Derivates

Figure 3:
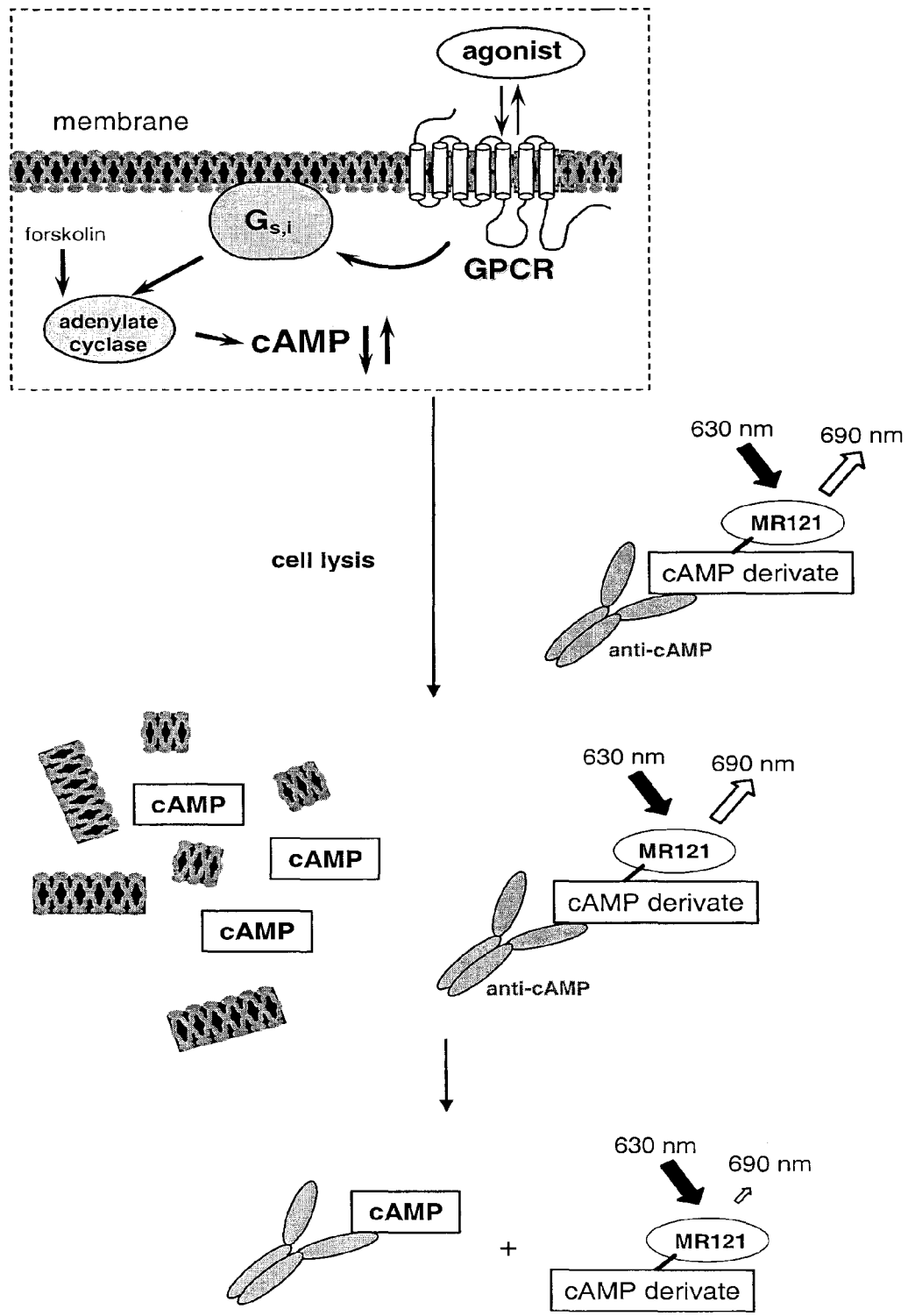
FIG. 3 shows a schematic representation of the assay principle with the example of determining cAMP concentration in a cell. The cells are lysed and a detection mix is added to the cell lysates. The detection mix comprises a complex of a fluorophore (e.g. MR121) linked to a cAMP quencher (cAMP derivate, e.g. 2-AHA-cAMP) and cAMP antibody (e.g. mouse monoclonal anti-cAMP antibody). The quenching effect of the quencher on the fluorophore is revoked by antibody (=dequencher). When contacted with cAMP, the antibody binds it instead of the cAMP derivate. Without the dequenching effect of the antibody, the cAMP quencher quenches the fluorophore and causes a decrease of fluorescent signal. The higher the cAMP concentration, the lower is the fluorescence.
Figure 4:
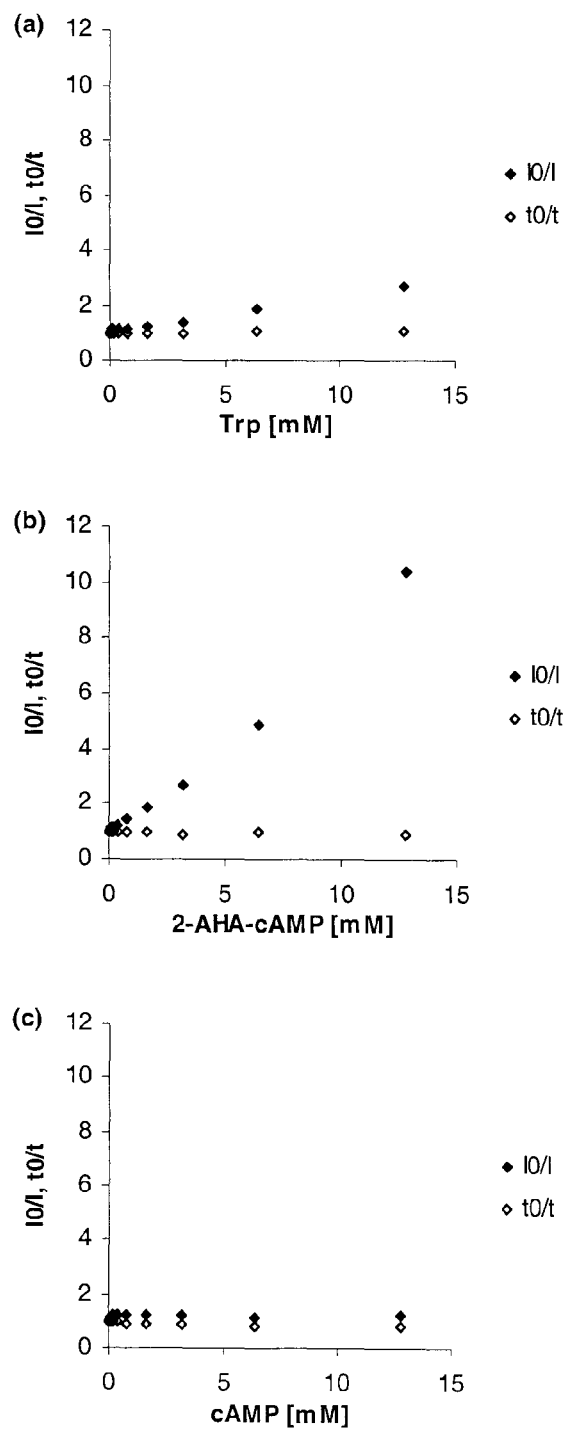
FIG. 4 shows a graphical representation of Stern-Volmer-Plots of MR121 and Tryptophane (a), 2-AHA-cAMP (b) and cAMP (c). $I_0/I$: change in fluorescence intensity ($I_0$ fluorescence intensity in the absence and I in the presence of a quencher), $t_0/t$: change of lifetime of the fluorescence ($t_0$ fluorescence lifetime in the absence and t in the presence of a quencher).

In order to analyze the quenching mechanism, measurements of fluorescence intensity and fluorescence lifetime of free MR121 as a function of different molecules (Trp, cAMP, 2-AHA-cAMP, 8-AHA-cAMP, 8-ADOA-cAMP, 2'-AEC-cAMP, N-6-Aminohexyl-cAMP, 8-MBT-cAMP and 8-OH-cAMP, see FIG. 4, 5) were carried out.

20 µl MR121 (in PBS, end concentration 20 nM) and 20 µl quencher in PBS (DMSO end concentration in the assay: 1.25%) were pipetted into a microtiter plate. Fluorescence and lifetime were measured after an incubation time of 30 minutes at RT. A decrease in fluorescence intensity without a change in fluorescence lifetime is observed with Trp. Surprisingly the decrease of fluorescence intensity is even more pronounced for 2-AHA-cAMP, 8-AHA-cAMP, 8-ADOA-cAMP, 8-MBT-cAMP and 8-OH-cAMP (with constant fluorescence lifetime) while cAMP, 2'-AEC-cAMP and N-6-Aminohexyl-cAMP show no quenching at all. In analogy to references 2-5 we conclude that MR121 forms a non-fluorescent ground state complex with 2-AHA-cAMP, 8-AHA-cAMP, 8-ADOA-cAMP, 8-MBT-cAMP and 8-OH-cAMP but not with cAMP, 2'-AEC-cAMP and N-6-Aminohexyl-cAMP.

In 2-AHA-, 8-AHA-, and 8-ADOA-cAMP the linker is coupled via an amine bond, in 8-MBT-cAMP via a sulfur and in 8-OH-cAMP via an oxygen bond directly to the purine ring system of adenosine. However in N-6-Aminohexyl-cAMP and 2'-AEC-cAMP the linker is coupled either to the amine group or the ribose moiety of adenosine. Apparently the modification of the adenosine leads to a change in the electronic states of the ring system which then favors the complex formation with the oxazine dye.

Figure 5:
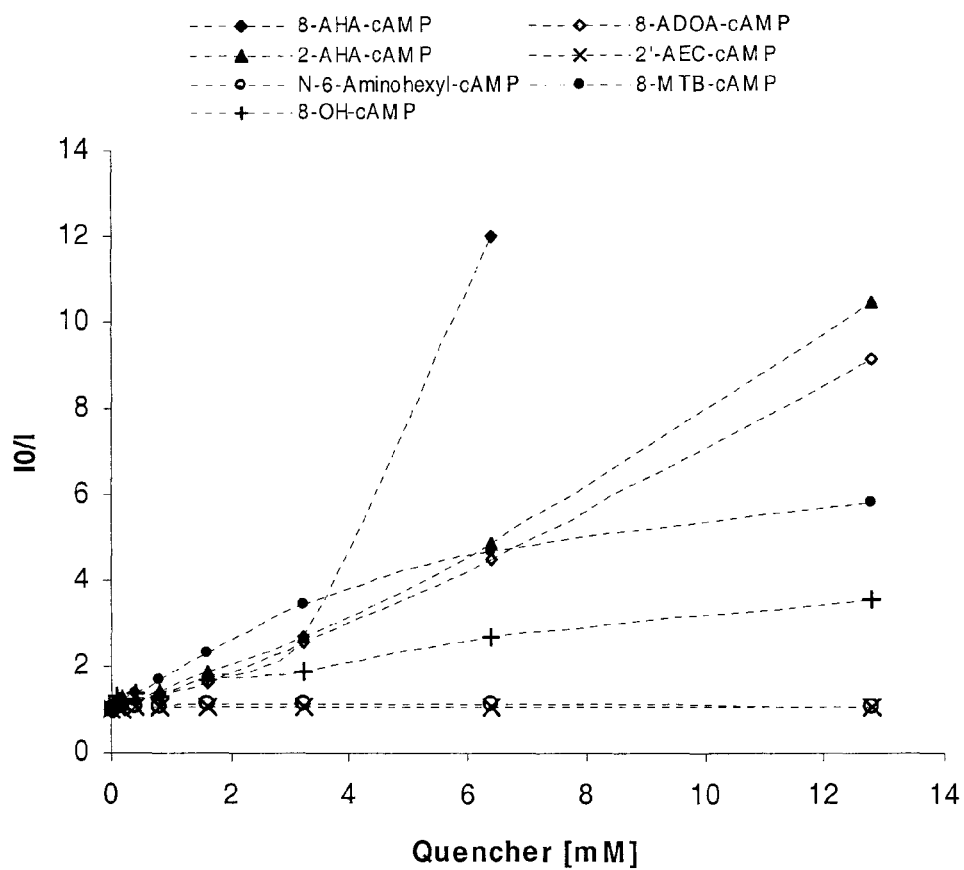
FIG. 5 shows a graphical representation of the decrease of fluorescence intensity ($I_0/I$) for different cAMP derivatives (8-AHA-cAMP, 2-AHA-cAMP, N-6-Aminohexyl-cAMP, 8-OH-cAMP, 8-ADOA-cAMP, 2'-AEC-cAMP, 8-MBT-cAMP). The large deviation from linearity for 8-AHA-cAMP above ~5 mM is due to solubility problems. $I_0/I$: change in fluorescence intensity

In FIG. 5 the change in fluorescence intensity (I$_0$/I) is plotted for all cAMP derivatives investigated. The association constant, K$_s$, was calculated from the linear region (up to 3.2 mM) of the plot giving 514 M$^{-1}$, 475 M$^{-1}$, 512 M$^{-1}$, 758 M$^{-1}$ and 236 M$^{-1}$ for 8-AHA-cAMP, 8-ADOA-cAMP, 2-AHA-cAMP, 8-MBT-cAMP and 8-OH-cAMP, respectively. This quenching is very efficient, the K$_s$ for most of the cAMP derivatives is more than twice compared to tryptophane reported in the literature (~220 M$^{-1}$).

Figure 6:
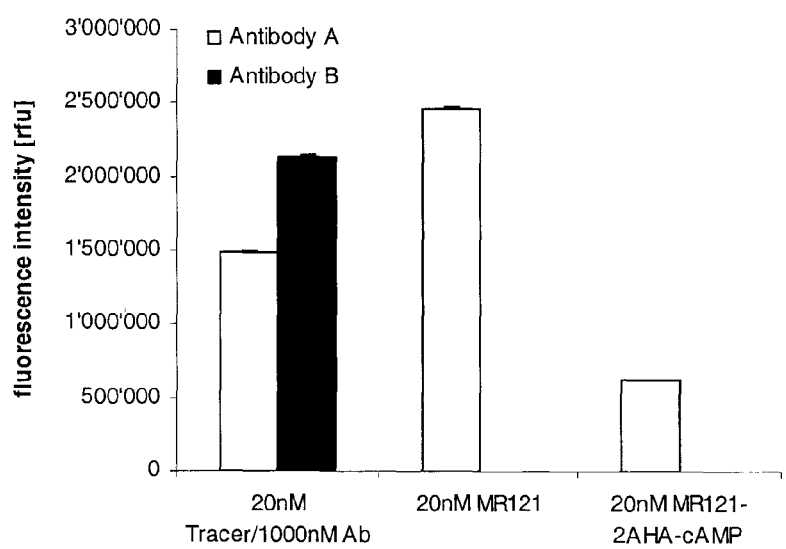
FIG. 6: shows a graphical representation of the quenching and dequenching of the fluorescence of the tracer MR121-2-AHA-cAMP using two different specific cAMP antibodies A and B. Ab: Antibody

When MR121-2-AHA-cAMP is bound to a specific cAMP antibody this non-fluorescent complex cannot be formed and an increase in MR121 fluorescence intensity is observed (FIG. 6). The fluorescence intensity of 20 nM free MR121, 20 nM MR121-2-AHA-cAMP (maximum quenching) and a mixture of 20 nM MR121-2-AHA-cAMP and 1000 nM antibody (maximum dequenching) was measured in PBS containing 0.1% BSA.

Compared to free MR121 (100%) the tracer shows a fluorescence intensity of 25%. Antibody A dequenches the fluorescence to 61%, antibody B to 87%. Apparently the degree of dequenching also depends on the binding affinity of the anti-cAMP antibody and on the amino acid sequence forming the binding domain of the antibody. A tryptophane in proximity to the binding domain of the antibody may quench the MR121 fluorescence to a certain degree. This can explain that different antibodies show different degrees of dequenching.

For the assay it is crucial that the antibody recognizes the tracer which is a labeled and modified cAMP and "pure" cAMP produced in the cells. For the further development of the assay we used antibody A although the dequenching is less compared to antibody B. However, the displacement of the tracer with cAMP is better with antibody A and the window full quenching—full dequenching is still good enough to develop a robust assay.

Example 2

K$_d$ Determination of Anti-cAMP Antibody

Figure 7:
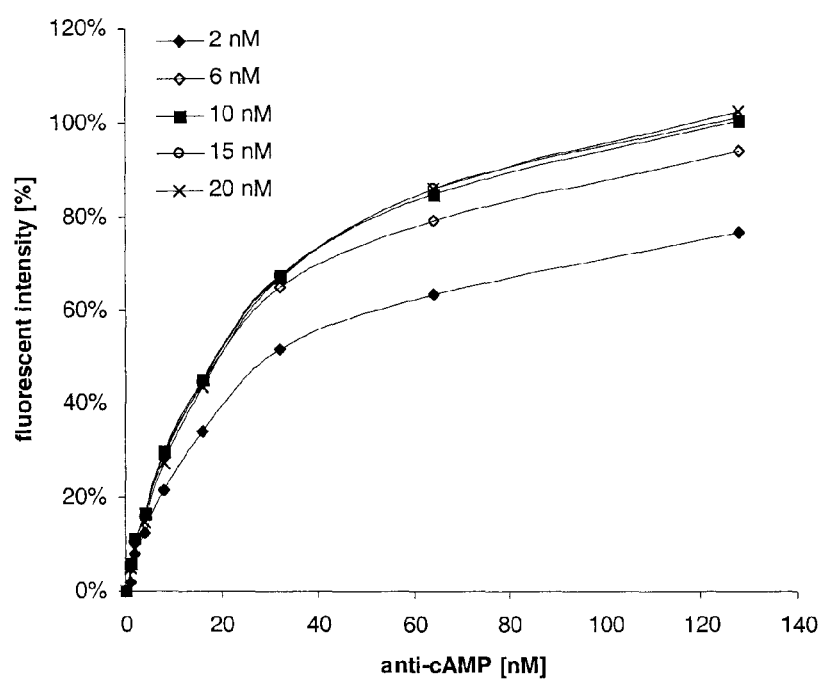
FIG. 7 shows a graphical representation of the titration of the anti-cAMP antibody at a fixed tracer concentration (10 nM MR121-2-AHA-cAMP). A fit of the experimental data resulted in a $K_d$ value of 28 nM.

The binding affinity of the anti-cAMP antibody (antibody A) to MR121-2-AHA-cAMP (K$_d$) was determined by titrating the antibody against several tracer concentrations (2, 6, 10, 15 and 20 nM) in 1× lysis buffer. 20 µl anti-cAMP dilutions were pipetted in 4 replicates into a 384 well microtiter plate. Then 20 µl MR121-2-AHA-cAMP were added to each well and the fluorescence intensity was read after 30 minutes incubation at RT on a 384 well shaker. The data were normalized by setting the values without antibody to 0%. FIG. 7 shows the corresponding titration curves. Fitting to a four parameter model yields K$_d$ values from 25 to 29 nM for the different tracer concentrations.

Example 3

Dose Response Curves cAMP

Figure 8:
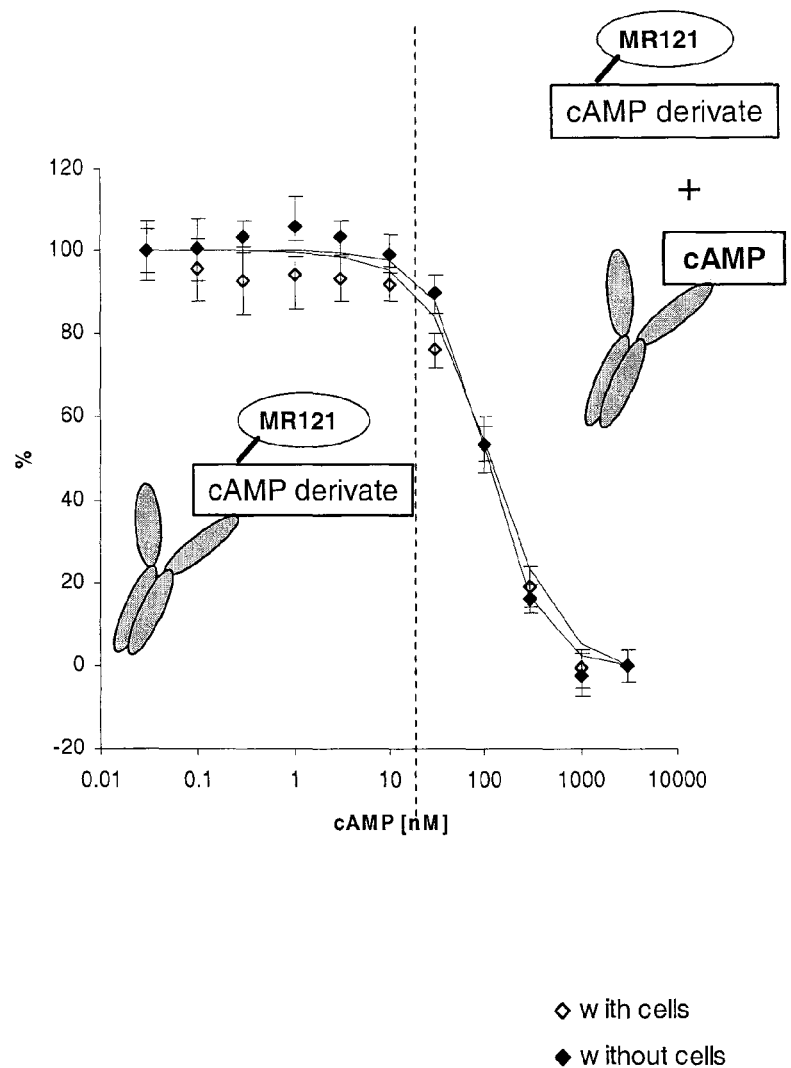
FIG. 8 shows a graphical representation of two cAMP standard curves, one without cells (filled diamonds) and one in the presence of cells (open diamonds), fitting of the curves gives $IC_{50}$=109 nM and 119 nM without and with cells, respectively.

Based on K$_d$=28 nM 40 nM anti-cAMP antibody and 20 nM MR121-2-AHA-cAMP were chosen for a sensitive detection of cAMP with an IC$_{50}$ around 100 nM. FIG. 8 displays two cAMP standard curves, one without cells and one with cells. For the standard curve without cells 20 µl cAMP dilutions in PBS containing 0.1% BSA were titrated into a 384 well microtiter plate and then 10 µl of the detection mix (120 nM anti-cAMP and 60 nM MR121-2-AHA-cAMP in 3× lysis buffer) were added. For the standard curve with cells 10'000 cells/well (CHO-K1) were plated in 25 µl medium and kept 20 h at 37° C. The medium was then removed and 20 µl cAMP dilutions in PBS+0.1% BSA followed by 10 µl detection mix were added. The plates were then incubated at RT on a 384 well shaker before reading the fluorescent signal. The determined IC$_{50}$'s are similar for both standard curves (109 and 119 nM without and with cells, respectively, see FIG. 8).

The stability of the cAMP standard curve with respect to time and to tolerability against DMSO and BSA were tested without cells using the detection mix in lysis buffer. With up to 5% DMSO and 0.8% BSA no change in $IC_{50}$ and no significant drop of signal were observed. Signal and $IC_{50}$ are stable for at least 6 h.

Figure 15:
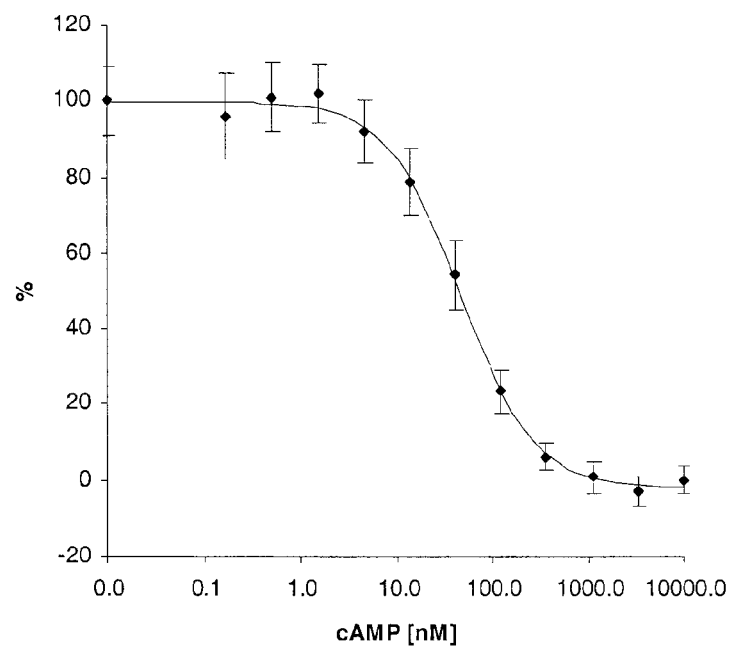
FIG. 15 shows a graphical representation of the decrease of fluorescence in relation to the concentration of cAMP (cAMP standard curve) with Atto700-2-AHA-cAMP as tracer and anti-cAMP antibody as dequencher. Fitting of the curve gives IC50=48 nM.

FIG. 15 shows a cAMP dose response curve done with 5 nM Atto700-2-AHA-cAMP tracer and 5 nM antibody giving an $IC_{50}$ of 48 nM. cAMP was diluted in PBS containing 0.1% BSA. 20 µl of the cAMP dilutions were titrated into a 384 well microtiter plate and 10 µl detection mix were added. The plate was incubated at RT on a 384 well shaker before reading the fluorescent signal.

cGMP

Figure 14:
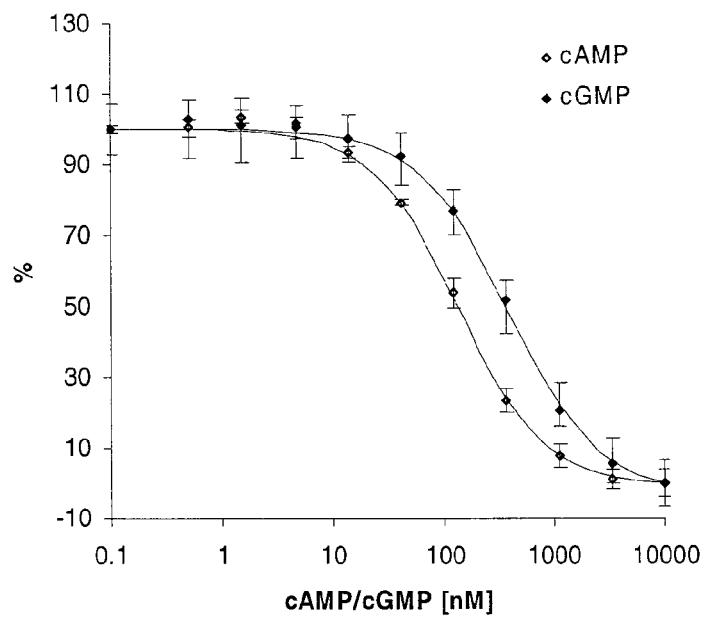
FIG. 14 shows a graphical representation of the decrease of fluorescence in relation to the concentration of cAMP and cGMP (standard curves).

FIG. 14 shows a comparison of the standard curves for cAMP and cGMP done with 20 nM MR121-2-AHA-cAMP tracer und 40 nM antibody giving an $IC_{50}$ of 134 nM for cAMP and 387 nM for cGMP. These $IC_{50}$ values as well as the sensitivity for cAMP and cGMP depend on the selection of the antibody. A different antibody may be more sensitive for cGMP and less sensitive for cAMP.

cAMP and cGMP were diluted in PBS containing 0.1% BSA. For the standard curve without cells 20 µl of cAMP dilutions and 20 µl cGMP dilutions were titrated into a 384 well microtiter plate and then 10 µl of the detection mix (40 nM anti-cAMP and 20 nM MR121-2-AHA-cAMP in 3× lysis buffer) were added. The plates were then incubated at room temperature on a 384 well shaker before reading the fluorescent signal.

Example 4 cAMP Cellular Assay

Figure 9:
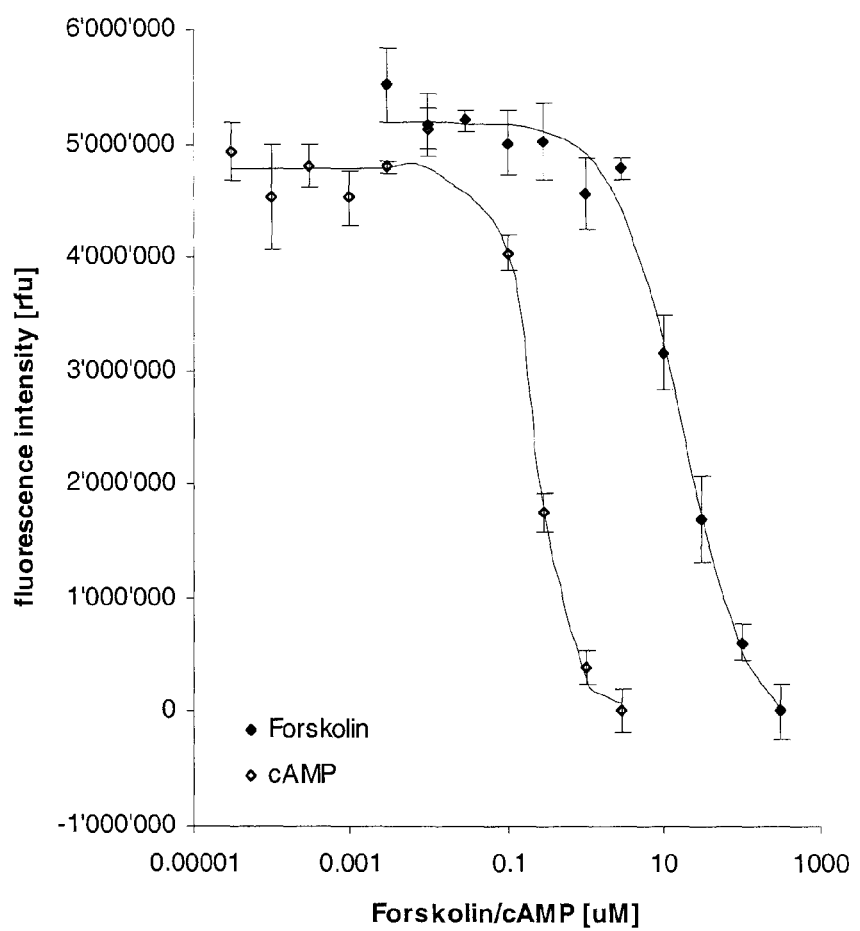
FIG. 9 shows a graphical representation of a Forskolin dose response curve and a cAMP standard curve with 10'000 cells/well, fitting of the curves gives $IC_{50}$=102 nM for cAMP and 3.7 µM for forskolin.

A forskolin dose response curve was performed with CHO-K1 cells. Cell numbers from 2, 500 to 20, 000 cell/well were plated in 25 µl medium and incubated for 20 h at 37° C. The medium was removed and after adding 10 µl of PBS with 0.1% BSA and 1 mM IBMX the cells were incubated for 60 minutes at 37° C. 10 µl of forskolin dilutions in PBS+0.1% BSA+1 mM IBMX from 0.01 to 300 µM (final concentration in 20 µl assay volume) were added and incubated for another 30 minutes at 37° C. Then the cells were lysed by adding 10 µl detection mix (20 nM MR121-2-AHA-cAMP+40 nM anti-cAMP, final concentration in 30 µl) in 3× lysis buffer and the fluorescence signal was read after 30 minutes incubation at RT on a 384 well shaker. With 10, 000 cells/well the maximal cAMP level and minimal $IC_{50}$ for Forskolin (3.7 µM) was reached. FIG. 9 shows a Forskolin dose response curve and a cAMP standard curve with 10, 000 cells/well.

Example 5

Quenching of ATTO590 and ATTO655

20 µl ATTO590 and ATTO655 respectively (in PBS, end concentration 20 nM) and 20 µl quencher (8-AHA-cAMP) in PBS (DMSO end concentration in the assay: 1.25%) were pipetted into a microtiter plate. Fluorescence and lifetime were measured after an incubation time of 30 minutes at RT. The results were incorporated in a Stern-Vollmer-Plot. The association constant, $K_s$, was calculated from the linear region (up to 3.2 mM) of the plot.

Figure 10:
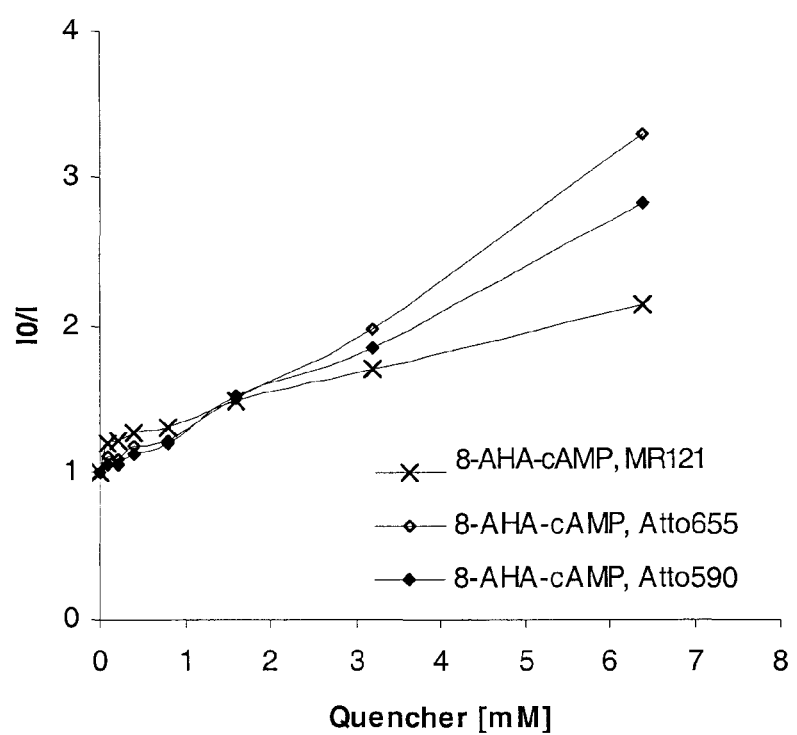
FIG. 10 shows a graphical representation of Stern-Vollmer Plots of the following molecules: MR121-8-AHA-cAMP, ATTO590-8-AHA-cAMP and ATTO655-8-AHA-cAMP.

Atto590 and Atto655 are quenched by 8-AHA-cAMP with $K_s=282$ $M^{-1}$ and $K_s=347$ $M^{-1}$, respectively (FIG. 10).

The invention claimed is:

1. An in vitro method for detecting cAMP (cyclic adenosine monophosphate) or cGMP (cyclic guanosine monophosphate), comprising the steps of:

a) contacting a mixture comprising cAMP or cGMP with a complex of a tracer and a dequencher, wherein
  i. the tracer is a single fluorophore covalently linked to a cAMP quencher,
  ii. the cAMP quencher is 2-AHA-cAMP (2-(6 aminohexyl) amino-adenosine-3'5'-cyclic monophosphate);
and wherein further the cAMP quencher quenches the fluorophore it is covalently linked to and the dequencher binds the cAMP quencher as well as the cAMP or cGMP in the mixture, and
b) measuring the change in fluorescence; wherein the covalently linked fluorophore linked to the cAMP quencher complex quenched the fluorescence emission; and wherein the measured change of fluorescence is compared with a control; and
wherein the fluorophore is;

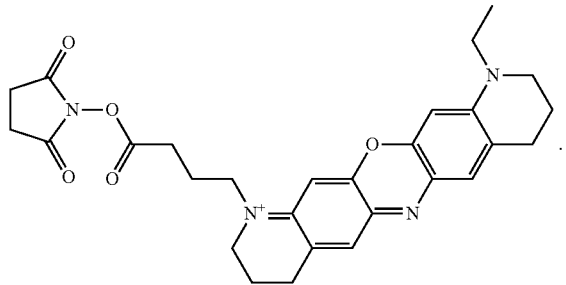 [SMILES: CCN1CCCc2cc3c(cc21)Oc1cc2c(cc1=N3)CCC[N+]=2CCCC(=O)ON1C(=O)CCC1=O]

2. An in vitro method for determining the activity of a receptor wherein the signal transduction of the receptor comprises cAMP or cGMP, comprising the steps of:

a) contacting cells expressing said receptor with a complex of a tracer and a dequencher, wherein the tracer is a single fluorophore covalently linked to a cAMP quencher and the cAMP quencher is selected from the group consisting of 2-AHA-cAMP;
  wherein further the cAMP quencher quenches the fluorophore it is covalently linked to and the dequencher binds the cAMP quencher as well as the cAMP or cGMP in the mixture;
b) lysing the cells;
c) measuring the change in fluorescence, wherein the measured change of fluorescence is compared with a control; and
wherein the fluorophore is;

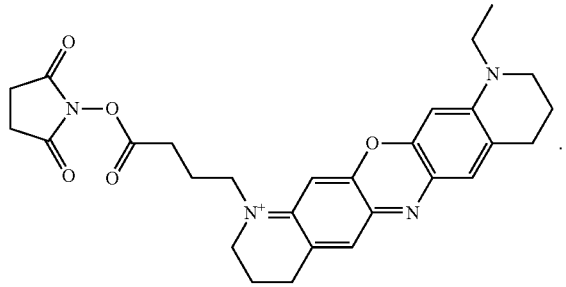 [SMILES: CCN1CCCc2cc3c(cc21)Oc1cc2c(cc1=N3)CCC[N+]=2CCCC(=O)ON1C(=O)CCC1=O]

3. An in vitro method for screening of a ligand for a receptor wherein the signal transduction of the receptor comprises cAMP or cGMP, comprising the steps of:

a) contacting a candidate compound selected to be tested for a receptor binding with a cell expressing said receptor
b) adding to the cells a complex of a tracer and a dequencher, wherein the tracer is a single fluorophore covalently linked to a cAMP quencher and the cAMP quencher is selected from the group consisting of 2-AHA-cAMP;
   wherein further the cAMP quencher quenches the fluorophore it is covalently linked to and the dequencher binds the cAMP quencher as well as the cAMP or cGMP in the mixture;
c) lysing cells,
d) measuring the change in fluorescence, wherein the measured change of fluorescence is compared with a control; and
   wherein the fluorophore is;

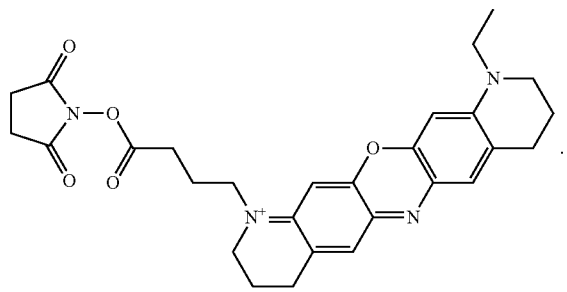 [SMILES: CCN1CCCc2cc3c(cc21)Oc1cc2c(cc1=N3)CCC[N+]=2CCCC(=O)ON1C(=O)CCC1=O]

4. An in vitro method for detecting cAMP car cGMP, comprising the steps of:
   a) contacting a mixture comprising cAMP or cGMP with a complex of a tracer and a dequencher, wherein
      i. the tracer is a fluorophore covalently linked to a cAMP quencher,
      ii. the cAMP quencher is 2-AHA-cAMP;
   and wherein further the cAMP quencher quenches the fluorophore it is covalent linked to and the dequencher binds the cAMP quencher as well as the cAMP or cGMP in the mixture, and
   b) measuring the change in fluorescence, wherein the measured change of fluorescence is compared with a control, and wherein the fluorophore is;

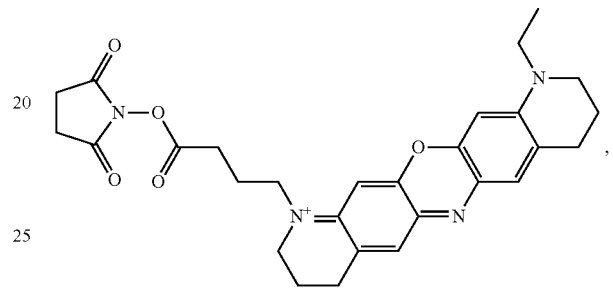

wherein the dequeneher is an antibody and wherein further step b) is performed without a washing step.

* * * * *